United States Patent [19]

Alderman et al.

[11] Patent Number: 4,678,516

[45] Date of Patent: Jul. 7, 1987

[54] SUSTAINED RELEASE DOSAGE FORM BASED ON HIGHLY PLASTICIZED CELLULOSE ETHER GELS

[75] Inventors: l Daniel A. Alderman; Troy D. Wolford, both of Midland, Mich.

[73] Assignee: The Dow Chemical Company, Midland, Mich.

[21] Appl. No.: 658,964

[22] Filed: Oct. 9, 1984

[51] Int. Cl.[4] .................. A61K 31/715; A61K 31/405
[52] U.S. Cl. .............................. 106/197.1; 106/15.05; 106/186; 106/188; 106/189; 424/DIG. 14; 424/DIG. 15; 424/488; 514/781; 514/966; 514/967
[58] Field of Search ............. 424/19, 28, 22, DIG. 15, 424/DIG. 14; 514/966, 967, 781; 106/186, 188, 189, 197.1, 15.05

[56] References Cited

U.S. PATENT DOCUMENTS

| | | | |
|---|---|---|---|
| 3,065,143 | 11/1962 | Christensen et al. | 424/35 |
| 4,140,756 | 2/1979 | Gallian | 424/19 |
| 4,155,993 | 5/1979 | Belleville | 424/19 |
| 4,259,314 | 3/1981 | Lowery | 424/19 |
| 4,265,875 | 5/1981 | Byrne et al. | 424/19 |
| 4,369,172 | 1/1983 | Schor et al. | 424/19 |
| 4,528,125 | 7/1985 | Alderman et al. | 426/651 |

FOREIGN PATENT DOCUMENTS 58-59910 4/1983 Japan.
59-216822 12/1984 Japan.

*Primary Examiner*—Ronald W. Griffin

[57] ABSTRACT

A solid sustained release dosage form is disclosed comprising a gel matrix containing HPMC and a major amount of a plasticizer therefor into which gel matrix is reversibly dispersed a pharmaceutically active agent.

14 Claims, No Drawings

SUSTAINED RELEASE DOSAGE FORM BASED ON HIGHLY PLASTICIZED CELLULOSE ETHER GELS

BACKGROUND OF THE INVENTION

This invention relates to a thermoplastic matrix for the controlled or sustained release of active organic materials, more particularly to a thermoplastic water-soluble matrix for the sustained release thereof.

The object of much research in recent years has been to provide sustained release dosage forms for various active organic materials, especially pharmaceuticals. For example, many active organic materials such as insecticides, herbicides, flavorings and the like are volatile or easily degraded in the environment in which they are employed. A sustained release form for such organic materials could reduce the volatilization or degradation by releasing only small amounts of the organic material, thereby keeping the level of organic material near the optimum amount needed to be effective. Thus, large excesses of the organic material do not volatilize or degrade before it performs its intended function.

Pharmaceuticals are of especial interest for sustained release applications. Most pharmaceuticals have a rather narrow therapeutic range in which they are of optimum benefit. Above or below this range, the drug is ineffective and/or is toxic. In administrating a tablet or capsule of the drug, the concentration thereof in the body may at first exceed therapeutic levels. Drug concentration then gradually decreases with time, until it falls below the therapeutic range. Thus, the time during which the drug is present in effective amounts may be quite short.

Sustained release or controlled release dosage forms are of interest because they can deliver and maintain optimum therapeutic levels of a medicament for a longer period of time than a conventional dosage form. In addition, such dosage forms can often deliver the medicament without an initial release of a greater than therapeutic amount thereof. An additional advantage is that by using a sustained release form, it is often possible to increase the time between successive administrations of the medicament, in effect reducing the frequency of administration.

Various sustained release dosage forms have been developed using cellulose ethers as a release controlling component. In U.S. Pat. No. 3,065,142 to Christiansen et al. it is taught to prepare a compressed matrix from a mixture of a powder methylcellulose or hydroxypropyl methylcellulose and an active medicament. Similar technology is also disclosed in U.S. Pat. Nos. 4,369,172 and 4,389,393. This dosage form has found great utility as an oral dosage form, a rectal suppository or intravaginal device. Unfortunately, however, these dosage forms have some properties which tend to limit their utility. For example, such dosage forms sometimes provide a high initial release of medicament which may in some instances be undesirable. Moreover, since the matrices are not thermoplastic, the shape of such dosage forms is limited to those which can be prepared by compressing powdered cellulose ethers.

It is also known to sustain the release of organic materials by coating the material with a water-insoluble cellulose ether such as ethylcellulose, cellulose acetate phthalate, and the like. This approach has also been found to be useful in certain instances, but the coating process employed is expensive and the shape and manner of use of the product sustained release form are limited.

European Patent Publication No. 0050480 discloses a multiple layer sustained release dosage form for the delivery of prostaglandin. Such dosage form comprises outer release controlling layers of hydroxypropyl cellulose (HPC), a water-insoluble polymer such as polyvinyl acetate or cellulose acetate, and a minor amount of a plasticizer. This added release controlling layer optionally, but less preferably, contains a prostaglandin. This dosage form further contains a drug storing layer comprising a water-soluble polymer such as HPC, a prostaglandin and optionally a minor amount of a plasticizer in a water-insoluble polymer. In this system, the presence of a water-insoluble polymer is considered essential to provide controlled release of the prostaglandin.

Similarly, in European Patent Publication No. 0086093 there is disclosed a three-layer pharmaceutical dosage form. This form comprises outer layers of HPC and a minor amount of a plasticizer (optionally containing prostaglandin) and a middle drug storing layer comprised of a water-insoluble polymer, a water-soluble polymer such as polyvinylpyrrolidone or HPC, plasticizer and an organic acid. In this reference, the use of a water-insoluble polymer is considered necessary in order to provide a suitable sustained release dosage form. Moreover, this dosage form requires the formation of the respective film layers followed by lamination of the layers to form the final product. In addition, this dosage form is not said to be useful as other than a prostaglandin delivery system.

In view of the deficiencies of the previously known sustained release forms, it would be desirable to provide an inexpensive, easily prepared, matrix for the sustained release of organic materials.

SUMMARY OF THE INVENTION

The present invention is a matrix for the prolonged release of an active organic material. This matrix comprises (a) a thermoplastic, water-soluble, substantially non-aqueous gel matrix comprising a water-soluble hydroxypropyl methylcellulose homogeneously dispersed in a plasticizer which comprises a major amount of the weight of said gel matrix and (b) dispersed in said gel matrix, an active organic material.

In another aspect, the present invention is a thermoformable sustained release matrix for the prolonged release of an active organic material, which matrix comprises (a) a thermoplastic water-soluble gel comprising a water-soluble hydroxypropyl methylcellulose homogeneously dispersed in a major amount of the weight of said gel of a plasticizer for said hydroxypropyl methylcellulose at the proportions thereof present in said gel and (b) dispersed in said gel, an effective amount of an active organic material.

The matrix provides for excellent prolonged release of the active organic material contained therein, without releasing an initial high concentration thereof. The matrix is also thermoplastic and as such is readily formed into a variety of shapes suitable for various modes of administration.

DETAILED DESCRIPTION OF THE INVENTION

The dosage form of this invention comprises, as one component, a thermoplastic water-soluble gel matrix comprising a water-soluble HPMC homogeneously dispersed into a major amount of a plasticizer.

The HPMC used herein contains sufficient hydroxypropoxyl and methoxyl substitution to render it water-soluble. HPMC having a methoxy degree of substitution from about 0.8 to about 2.5 and a hydroxypropoxyl molar substitution from about 0.05 to about 3.0 are generally water-soluble. "Methoxy degree of substitution" (MDS) refers to the average number of methyl ether groups present per anhydroglucose unit of the cellulose molecule. "Hydroxypropoxyl molar substitution" (HPMS) refers to the average number of moles of propylene oxide which are reacted with each anhydroglucose unit of the cellulose molecule.

The molecular weight of the HPMC used herein is not especially critical as long as the HPMC forms a gel matrix with the plasticizer employed herein. However, the molecular weight of the cellulose ether does affect both the release profile of the matrix as well as its physical properties. As a general rule, the use of higher molecular weight HPMC causes them to have greater physical strength and a longer release profile. Thus, it is readily seen that the molecular weight of the HPMC is a parameter which is readily manipulated by the practitioner to achieve a desired release profile or physical property in the product matrix.

The molecular weight of a water-soluble cellulose ether is generally expressed in terms of the viscosity at 20° C. of an aqueous solution containing two percent by weight of the polymer. Suitable HPMC includes those having a viscosity from about 5 to about 100,000 centipoises. To obtain a dosage form providing a relatively fast release of active organic material and/or moderate physical strength, a HPMC having a viscosity of about 5–15,000, preferably 100–4,000 is suitable. For more prolonged release of active organic material and/or greater strength, a HPMC having a viscosity of about 15,000–100,000, preferably 15,000–75,000 is suitable. It should be noted that factors other than the particular HPMC employed also affect these properties. For example, an increasing amount of plasticizers extends to reduce the physical strength of the matrix and increase the rate of release of the active organic material.

When the matrix is a pharmaceutical dosage form to be taken internally has in a tablet, suppository or intravaginal device, the HPMC preferably is of a purity and grade suitable for consumption.

Preferred HPMC includes those having a MDS from about 1.8 to 2.0 and HPMS from about 0.2 to about 0.31 such as is commonly available under the tradenames Methocel ®  E Premium and Metalose ®  60SH; those having a MDS from about 1.1 to about 1.6 and a HPMS of 0.1 to 0.3 such as are commercially available under the tradenames Methocel ®  K Premium and Metalose ®  90SH; and those having a MDS from about 1.1 to 1.5 and a HPMS from about 0.7 to 1.0 such as are commercially available under the tradename Methocel ®  J. Methocel products are available from The Dow Chemical Company and Metalose products are available from Shin-etsu Chemical Company, Ltd. Japan.

The gel matrix further comprises a plasticizer for the HPMC. The plasticizer employed herein is a material which (a) reduces the softening point of the HPMC below its decomposition temperature and desirably (b) imparts more desirable physical properties to the gel matrix. A further characteristic of the plasticizer is that it is compatible with the HPMC at the relative proportions thereof present in the matrix. By "compatible" it is meant that a substantially homogeneous dispersion or solution of the HPMC in the plasticizer is made with little or no tendency for the HPMC and plasticizer to phase separate.

Preferably, the plasticizer employed herein is also a solvent for the HPMC at the elevated temperature at which the dosage form is prepared. Such plasticizer, when mixed with the HPMC above a characteristic temperature at which the HPMC becomes soluble therein, dissolves the HPMC. Upon cooling, the mixture forms a gel matrix having especially useful properties for use in a sustained release dosage form.

Suitable plasticizers include low molecular weight polyols having aliphatic hydroxyls such as ethylene glycol; propylene glycol; 1,2-butylene glycol; 2,3-butylene glycol; styrene glycol; polyethylene glycols such as diethylene glycol, triethylene glycol, tetraethylene glycol and other polyethylene glycols having a molecular weight of about 1,000 or less; polypropylene glycols of molecular weight 200 or less; glycol ethers such as monopropylene glycol monoisopropyl ether; propylene glycol monoethyl ether; ethylene glycol monoethyl ether; diethylene glycol monoethyl ether; ester-type plasticizers such as sorbitol lactate, ethyl lactate, butyl lactate, ethyl glycolate, allyl glycolate; and amines such as monoethanolamine, diethanolamine, triethanolamine, monisopropanolamine, triethylenetetramine, 2-amino-2-methyl-1,3-propanediol and the like. Of these, the low molecular weight polyethylene glycols, ethylene glycol, low molecular weight polypropylene glycols and especially propylene glycol are preferred.

The plasticizer is employed herein in an amount sufficient to render the matrix thermoformable. Typically, the plasticizer will comprise a major amount of the weight of the matrix, i.e., at least about 30% by weight. Preferably, the plasticizer comprises from about 30 to 95 percent of the combined weight of plasticizer and HPMC. The amount of plasticizer present in the matrix very substantially affects its properties. A more flexible matrix is obtained when a relatively high level of plasticizer, i.e., 50–90%, is present therein. The use of a lesser amount of plasticizer (i.e. 30–50%, preferably 40–50%) provides a stiffer, harder matrix.

The matrix of this invention further contains at least one active organic material which is capable of being released in active form from the matrix under the conditions at which the matrix is used. Preferably, the active organic material is heat stable, i.e., capable of being heated to a temperature sufficient to prepare a gel matrix from the HPMC and the plasticizer without being rendered inactive.

The active organic material may be, for example, a herbicide, insecticide, nematocide, fungicide, antimicrobial or other biocides, a medication, vitamin, coloring, preservative or any other organic compound or mixture of organic compounds which is advantageously controllably released into the system to be treated therewith. As long as the active organic material can become reversibly diffused, either alone, in a solution, or with the use of a compatibilizing agent, into the cellulose ether particles, its structure is not especially critical. Suitable active organic materials range from comparatively simple molecules, like carbon tetrachloride to complex molecules such as vitamins.

Exemplary herbicides include, for example, alkanolamine salts of dinitro-o-sec-butylphenol, propylene glycol butyl ethers of 2-(2,4,5-trichlorophenoxy)-propanolic acid, chlorinated phenoxy acetic acid and salts or esters thereof, salts of 4-amino-3,5,6-dichloropicalinic acid, as well as many other commercially available herbicides.

Suitable insecticides include, for example, chlorpyrifos(O,O-dialkyl-O-(3,5,6-trichloro-2-pyridyl)phosphorothioate), fenchlorphos-(O-O-dialkyl-O-(2,4,5-trichlorophenyl)phosphorothioate) and the like.

Suitable fungicides include 1,3-dichloropropene, trichloronitromethane (chloropicrin), mixtures thereof and the like.

Exemplary preservatives include the phenylphenols, chlorinated phenylphenols, chlorinated phenols, cyclopentylphenols, hexamethylenetetraamine-1,3-dichloropropane salt, as well as others.

Any of the commonly employed organic flavorants are suitably employed herein, including, for example, orange oil, lime oil, cherry oil, lemon oil, peppermint oil, spearmint oil, wintergreen oil, licorice and other spices and fruit flavors.

Suitable pharmaceutically active agents include antacids, anti-inflammatory substances, coronary vasodilators, cerebral vasodilators, peripheral vasodilators, anti-infectives, psychotopics, antimanics, stimulants, antihistamines, laxatives, decongestants, vitamins, gastrointestinal sedatives, antidiarrheal preparations, antianginal drugs, antiarrhythmics, antihypertensive drugs, vasoconstrictors, migraine treatments, anticoagulants, antithrombotic drugs, analgesics, antipyretics, hypnotics, sedatives, anti-emetics, antinauseants, anticonvulsants, neuromuscular drugs, hyper- and hypoglycaemic agents, thyroid and antithyroid preparations, diuretics, antispasmodics, uterine relaxants, mineral and nutritional additives, antiobesity drugs, anabolic drugs, erythropoietic drugs, antiasthmatics, expectorants, cough suppressants, mucoltics, antiuricemic drugs and other drug substances such as topical analgetics, local anaesthetics and the like.

If an oral dosage form is contemplated, the pharmaceutically active agent is of a type which acts orally in the mouth or which can be administered orally to transmit the pharmaceutically active agent in active form to gastrointestinal tract. Similarly, if the dosage form is a suppository or intravaginal device the drug is one which acts locally or which may be transmitted in active form through the adjacent tissues.

In addition to the foregoing critical components, various optional ingredients such as are conventionally used in the art, may be employed in the matrix of this invention. For example, colorings, flavorings, sweeteners, fragrances, diluents, fillers, preservatives, anti-oxidants, stabilizers, lubricants, and the like may be employed herein if desired. Also, a minor amount of additional water soluble or insoluble polymers, such as hydroxypropylcellulose, carboxymethylcellulose, methylcellulose, ethylcellulose, polyvinyl pyrrolidones, and the like may optionally be used herein. When such optional polymer is used, it does not exceed about 50% by weight of the weight of the HPMC used herein. The use of such optional polymers is not generally required or preferred herein, but may in certain instances be useful in providing a particular rate of release of the active agent.

The matrix of this invention can be prepared by mixing together the HPMC, plasticizer and phamaceutically active agent under conditions sufficient to homogeneously disperse the HPMC into the plasticizer.

As described hereinbefore, the preparation of the matrix is advantageously conducted at an elevated temperature. When elevated temperatures are used, it is important to select a temperature at which the active organic material is stable, or if a higher temperature is desired to minimize the time during which the organic material is exposed to such temperatures in order to minimize degradation thereof. Mixing is accomplished in conventional manner using any suitable apparatus until the HPMC is homogeneously dispersed into the plasticizer.

As stated hereinbefore, a plasticizer is preferably a material in which the HPMC becomes soluble at elevated temperatures. When such a plasticizer is used, the matrix is advantageously prepared by conducting the mixing step at a temperature at which the HPMC is soluble in the plasticizer, subject to the limitations described hereinbefore.

Following the mixing of the HPMC, plasticizer and active organic material, the resulting dispersion is cooled to form a matrix into which the active organic material is reversibly dispersed.

Because of the thermoplastic nature of the matrix of this invention, it is readily thermoformed into any desirable shape for use. For example, the matrix is conveniently shaped into tablets, prills, lozenges and the like for use as an oral pharmaceutical dosage form. If desired, the matrix may be shaped into prills and placed in conventional gelatin capsules. Intravaginal devices and suppositories are readily formed by shaping the matrix of this invention. Diverse complexly shaped matrixes of this invention are readily prepared to meet a wide variety of functional requirements. Shaping can be affected, for example, by injection molding, compression molding, extrusion, hot dipping, melt casting and like techniques.

The following examples are provided to illustrate the invention but not to limit the scope thereof. All parts and percentages are by weight unless otherwise indicated.

EXAMPLE 1

To 75 parts propylene glycol are added at ambient temperature 25 parts of an HPMC sold commercially as Methocel E4M Premium (available from The Dow Chemical Company). To 95 parts of this mixture are added 5 parts riboflavin. The resulting mixture is stirred briefly and fed into a Haake ¾ inch extruder. The temperature of the extruder zones are 120° C., 125° C., 130° C. and 120° C. During the movement of the mixture through the extruder, the mixture becomes more viscous as the temperature rises and the polymer goes into solution. Dissolution of the HPMC into the propylene glycol occurs at about 105° C. The resulting extrudate is a flexible rope matrix of substantial strength. A one-gram section of said extrudate is put into a dissolution apparatus and evaluated according to the standard USP test dissolution method with 0.1N HCL as the dissolution medium and at a paddle speed of 100 rpm. The rate of release of riboflavin from this sample (hereinafter referred to as Sample I-A) is provided in Table I following.

Sample No. I-B is prepared in like manner, this time employing 50 parts of the HPMC and 50 parts of proylene glycol. The matrix exhibits a dissolution profile as reported in Table I following.

TABLE I

| Amount of Drug Released | Elapsed Time to Release Drug (Hours) | |
|---|---|---|
| | Sample No. I-A | Sample No. I-B |
| 10% | 0.5 | 1.0 |
| 20% | 1.2 | 2.0 |
| 30% | 2.2 | 3.0 |
| 40% | 3.1 | 5.0 |
| 50% | 4.5 | 7.1 |
| 60% | 6.0 | 9.6 |
| 70% | 8.1 | 13.1 |
| 80% | 11.0 | 17.5 |
| 90% | 14.8 | 23.7 |
| 100% | 23.6 | 32.0 |

As can be seen from the data presented in Table I, a very prolonged, regular release of active medicament is provided with the matrix of this invention.

EXAMPLE 2

In a manner similar to that described in Example 1, Sample No. II-A is prepared by mixing 75 parts by weight propylene glycol and 25 parts by weight of an HPMC having a MDS of 0.3–1.0, a HPMS of 1.1–1.6 and a 2% aqueous solution viscosity of 5000 centipoises. To 95 parts of this mixture are added 5 parts riboflavin. This mixture is extruded and tested as described in Example 1 with results as reported in Table II following.

Sample No. II-B is prepared in like manner, this time substituting a 20,000 centipoise HPMC for the 5000 centipoise material employed in Sample No. II-A. Similarly, Sample No. II-C is prepared, this time substituting a 40,000 centipoise NPMC for the 5000 centipoise material used in Sample No. IIA. The release profile of these samples are as described in Table II following.

TABLE II

| Amount of Drug Released | Elapsed Time to Release Drug (Hours) | | |
|---|---|---|---|
| | Sample No. II-A | Sample No. II-B | Sample No. II-C |
| 10% | 0.5 | 0.6 | 0.6 |
| 20% | 1.1 | 1.8 | 1.9 |
| 30% | 2.1 | 2.8 | 3.7 |
| 40% | 3.3 | 4.1 | 5.2 |
| 50% | 4.8 | 5.8 | 7.1 |
| 60% | 6.4 | 7.5 | 9.2 |
| 70% | 8.2 | 9.5 | 12.1 |
| 80% | 10.2 | 12.0 | 15.6 |
| 90% | 12.8 | 15.1 | 19.7 |
| 100% | 17.4 | 21.3 | 24.9 |

As can be seen from the results in Table II, each of Sample Nos. II-A, II-B and II-C provides excellent sustained release of riboflavin. These data also illustrate the effect of molecular weight on the release profile of the dosage form. The results reported in Table II show that a more prolonged release profile is provided with the higher molecular weight HPMC.

EXAMPLE 3

Sample No. III A is prepared by adding to 40 parts of a HPMC having an MDS of 1.1 to 1.6, a HPMS of 0.7–1.0 and a 2% aqueous solution viscosity of 15 centipoises, 5 parts dibromonitrilopropionamide (DBNPA) dissolved in 55 parts tetraethylene glycol. These components are stirred and extruded through a Haake Rheomex extruder at 80°–82° C. A flexible gel extrudate is obtained.

A 2.036 g sample of the extrudate is dissolved in sufficient water to form a 1% aqueous DBNPA solution. The solution is aged one day, at room temperature and then is incorporated into multiple nutrient agar plates at 10, 25, 50, 100, 250 and 500 ppm DBNPA. Each plate is inoculated with *Bacillus subtilis*, *Enterobacter aerogenes*, *Escherichia coli*, *Klebsiella pneumoniae*, *Proteus vulgaris*, *Pseudomonas aeruginosa*, *Salmonella choleraesius*, and *Staphylococcus aureus*. After incubation for 24 hours at 30° and refrigeration another 48 hours the growth of the bacteria is observed. The minimum inhibiting concentration for the gel matrix is found to be slightly better than that of DBNPA delivered from a standard tetraethylene glycol solution.

The experiment is repeated with Sample No. III-B, which is like Sample No. III-A except 47.5 parts each of HPMC and tetraethylene glycol are used. The minimum inhibitory concentration is generally equal to that of DBNPA delivered from a standard tetraethylene glycol solution. However, this test verifies the release of DBNPA in active form from the gel matrix.

What is claimed is:

1. A thermoformable sustained release matrix for the prolonged release of an active organic material, which matrix comprises (a) a thermoplastic water-soluble gel comprising a water-soluble hydroxypropyl methylcellulose homogeneously dispersed in an amount of a plasticizer for the cellulose ether sufficient to render the matrix thermoformable, and (b) dispersed in said gel, an effective amount of an active organic material.

2. The matrix of claim 1 wherein said plasticizer is a solvent for said hydroxypropyl methylcellulose at an elevated temperature.

3. The matrix of claim 2 wherein said active organic material is not rendered inactive at an elevated temperature in which the hydroxypropyl methylcellulose is soluble in said plasticizer.

4. The sustained release matrix of claim 2 wherein said hydroxypropyl methylcellulose has a hydroxypropoxyl molar substitution from about 0.05 to 3.0 and a methoxyl degree of substitution for about 0.8 to 2.5.

5. The matrix of claim 4 wherein said hydroxypropyl methylcellulose has a hydroxypropoxyl molar substitution for about 0.2 to 0.31 and a methoxyl degree of substitution from about 1.8 to 2.0.

6. The matrix of claim 4 wherein said hydroxypropyl methylcellulose has a hydroxypropoxyl molar substitution for about 0.1 to 0.3 and a methoxyl degree of substitution from about 1.1 to 1.6.

7. The matrix of claim 4 wherein said hydroxypropyl methylcellulose has a hydroxypropoxyl molar substitution for about 0.7 to 1.0 and a methoxyl degree of substitution from about 1.1 to 1.6.

8. The matrix of claim 2 wherein said plasticizer is ethylene glycol, a low molecular weight polyethylene glycol, propylene glycol or a low molecular weight propropylene glycol.

9. The matrix of claim 4 wherein the active organic material is a pharmaceutical.

10. The matrix of claim 9 which is an oral dosage unit.

11. The matrix of claim 4 which is a rectal suppository.

12. The dosage form of claim 4 which is a intravaginal dosage form.

13. The matrix of claim 4 wherein the active agent is an antimicrobial.

14. The sustained release matrix of claim 1, wherein the plasticizer comprises from about 30 to 95 percent of the combined weight of plasticizer and hydroxypropyl methylcellulose.

* * * * *